United States Patent [19]

Arms

[11] Patent Number: 5,083,573

[45] Date of Patent: Jan. 28, 1992

[54] METHOD OF AND MEANS FOR IMPLANTING A PRESSURE AND FORCE SENSING APPARATUS

[76] Inventor: Steven W. Arms, P.O. Box 86, Burlington, Vt. 05402

[21] Appl. No.: 655,045

[22] Filed: Feb. 14, 1991

Related U.S. Application Data

[63] Continuation-in-part of Ser. No. 478,426, Feb. 12, 1990, Pat. No. 4,993,428.

[51] Int. Cl.⁵ .............................................. A61B 5/103
[52] U.S. Cl. .................................................... 128/774
[58] Field of Search .................. 128/774, 782; 73/768, 73/779

[56] References Cited

U.S. PATENT DOCUMENTS

| | | | |
|---|---|---|---|
| 3,905,356 | 9/1975 | Fletcher et al. | 128/774 X |
| 4,204,544 | 5/1980 | Feldstein et al. | 128/642 |
| 4,294,015 | 10/1981 | Drouin et al. | 33/174 D |
| 4,813,435 | 3/1989 | Arms | 128/774 |
| 4,993,428 | 2/1991 | Arms | 128/774 |

Primary Examiner—Kyle L. Howell
Assistant Examiner—Kevin Pontius
Attorney, Agent, or Firm—Thomas N. Neiman

[57] ABSTRACT

This apparatus is adapted for replaceable implantation in soft body tissues for the measurement of the mechanical behavior of the soft tissues of the body. The apparatus consists of a thin walled tube containing a longitudinal slot down one side with at least one piezo-resistive strain gauge element bonded to its inner or outer walls. Tension in tissue fiber bundles results in a squeezing pressure against the sides of the tube, which produces a change in the shape of the tube and thus a change in the resistance of the strain gauge element. This resistance change is then measured and displayed. A method of inserting and removing the apparatus is also described, as are several techniques for calibration.

5 Claims, 2 Drawing Sheets

FIG. 3
FIG. 4
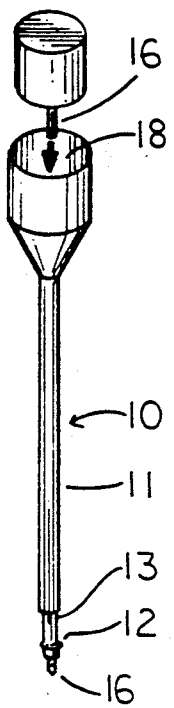
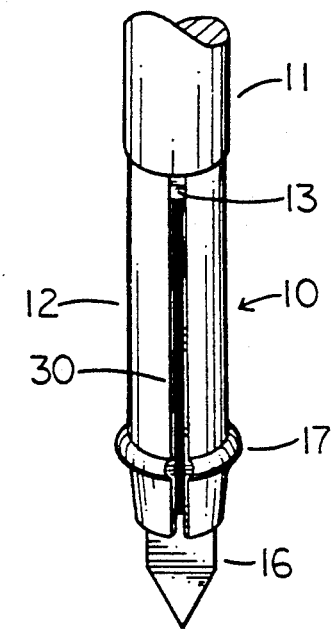
FIG. 5
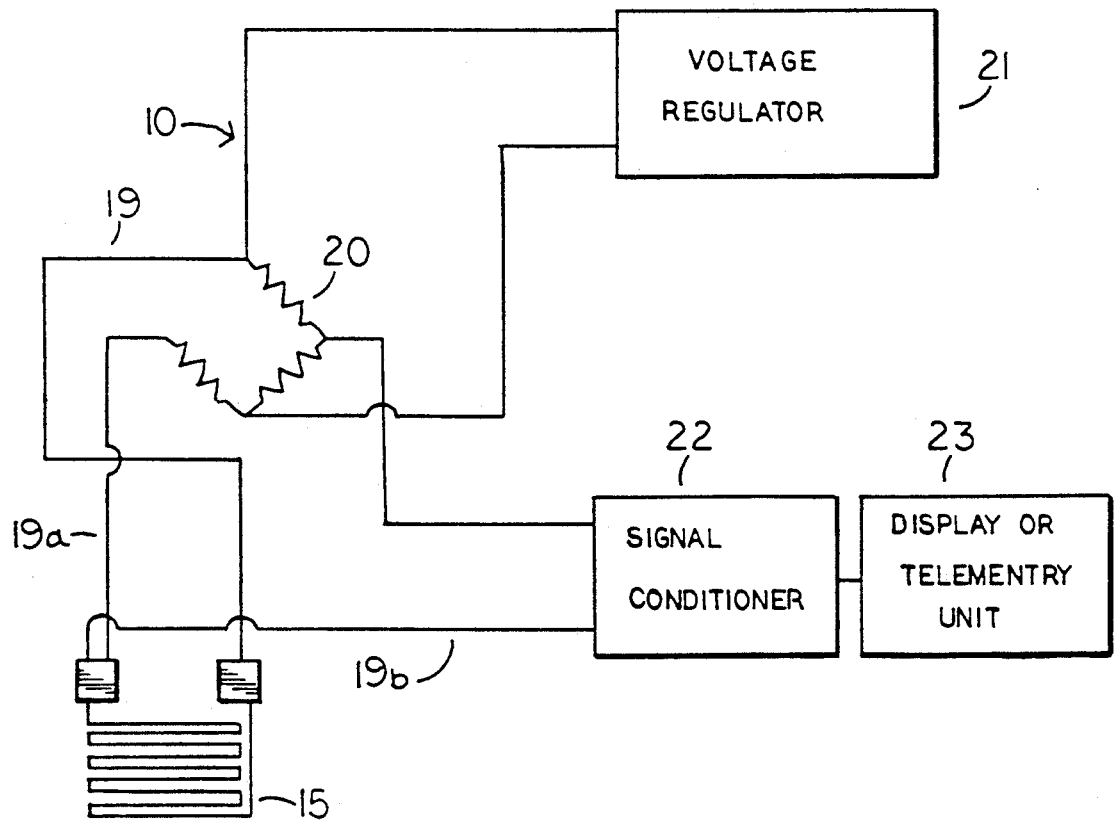

METHOD OF AND MEANS FOR IMPLANTING A PRESSURE AND FORCE SENSING APPARATUS

This is a continuation-in-part application on my co-pending application Ser. No. 07/478,426, filed on Feb. 12, 1990, which issued as U.S. Pat. No. 4,993,428 on the 19th of February 1991.

This invention pertains to medical measurement devices, and in particular to such medical measurement devices that relate to the measurement of the mechanical behavior of the soft tissues of the body by implanting a pressure and force sensing apparatus that can easily be implanted and removed as necessary.

Devices that measure the mechanical behavior of soft tissue are well known to those interested in the field of measuring the relative movement of individual parts of the body. The prior art contains many examples which pertain to measuring relative movement includes the U.S. Patent issued to Steven W. Arms for an Implantable Displacement Sensor Means, U.S. Pat. No. 4,813,435 issued on Mar. 21 1989. This device measures soft tissue tension by sensing the squeezing against the sides of the device. This device was an improvement over previous devices shown in the United States Patent issued to Gilbert Drouin, U.S. Pat. No. 4,294,015, issued on Oct. 13, 1981 for an Extensometer and the United States Patent issued to Paul H. Brace, U.S. Pat. No. 4,319,236 on Mar. 9, 1982 for a Hall Effect Position Detector. The main disadvantages of these devices are that they are not completely immersed in the soft tissue, and therefor, there can be interference from bone or overlying soft tissue structures.

The difficulties that are inherent in these designs and should be overcome include the following: large sizing of the equipment; the inability to insert the entire structure within the soft tissues; lack of the ability to use those devices during arthroscopic surgery.

Clearly, it is desirable for an apparatus for measuring pressure and forces within the soft tissues of the body to be developed. It is the object of this invention to set forth a method of and means for implanting a pressure and force sensing apparatus which avoids the disadvantages and limitations, above-recited, which occur in previous measuring devices. It is another object of this invention to teach a device that has a small geometry and provides a continuous readout for said means.

It is also the object of this invention to teach an apparatus for measuring the mechanical behavior of soft tissue which is simple to install and use and that will enable the surgeon to easily determine the exact placement of the apparatus in the soft tissue. Particularly, it is the object of this invention to set an implantable pressure and force sensing apparatus, for measuring the mechanical behavior of the soft tissue of the body, comprising a main guide cannulae; said main guide cannulae having an alignment key positioned at the lower end of said main guide cannulae; said main guide cannulae further having a direction indicator at the upper end of said cannulae; retractable centerline cutting and positioning means; tubular means comprising that fit over said retractable centerline cutting and positioning means; said tubular means having at least one sensing means attached thereto; said tubular means further having a longitudinal slot for receiving said alignment key of said main guide cannulae from one end of said tubular means to the opposite end of said tubular means; said tubular means further having an alignment projection means located at the upper end of said tubular means for maintaining said tubular means in proper orientation within the tissue; said upper end of said tubular means being in close replaceable contact with the lower end of said main guide cannulae for the purpose of buttressing said tubular means during implantation; and said tubular means further having an enlarged tapered section at the end opposite said upper end for preventing said tubular means from backing out of the tissue. Furthermore, it is the object of this invention to teach a method of implanting a pressure and force sensing apparatus, for use in medical and other applications, comprising the steps of providing a main guide cannulae which has an alignment key projecting therefrom; providing a retractable trocar; inserting the retractable trocar within the main guide cannulae; providing tubular means which has sensing means attached thereto; emplacing the tubular means over the trocar; positioning the alignment key in the longitudinal slot of said tubular means; pressing said trocar and said tubular means at the desired position on the soft tissue of the patient's body; cuttingly penetrating the soft tissue of a patient's body with said trocar and said tubular means until the desired depth, at which to implant the sensing means, has been reached; and using the cannulae as a buttressing element during the penetrating step; wherein said cannulae has a positioning arrow at one end thereof; and maintaining a proper positioning of the cannulae and alignment projection of the tubular means by reference to the arrow; removing the trocar from the cannulae; and removing the cannulae.

Further objects and features of this invention will become more apparent by reference to the following description taken in conjunction with the accompanying figures, in which:

FIG. 3 is a side view of the insertion means of the novel apparatus;

FIG. 4 is a perspective view of the novel apparatus from the opposite side from the view shown in FIG. 1;

FIG. 5 is a schematic block drawing of the voltage or current regulator, bridge circuit, signal conditioner and display.

Figure 1:
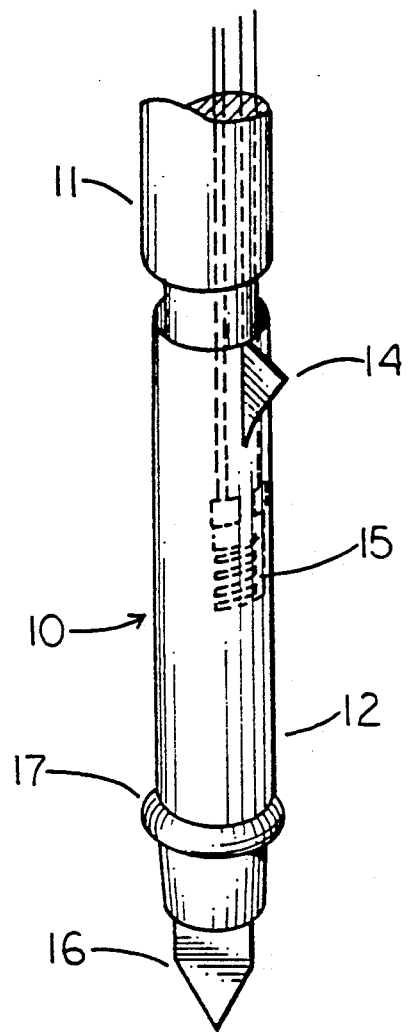
FIG. 1 is a perspective view of the novel pressure and force sensing apparatus.
Figure 6:
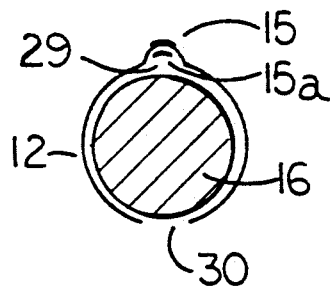
FIG. 6 is a cross-sectional view of the novel apparatus showing an alternative unit with two strain gauge elements, one inside and one outside the tube.
Figure 2:
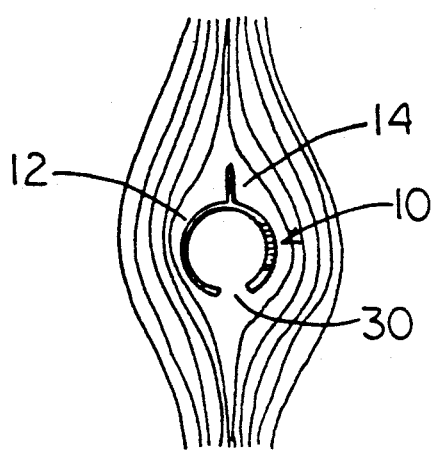
FIG. 2 is a top view of the novel apparatus in position.

As shown in the figures, the novel pressure and force sensing apparatus 10 is comprised of main guide cannulae 11 that contains an alignment key 13 located at the bottom end of the cannulae 11. A retractable trocar 16 fits inside the cannulae 11 and is used to cut the soft tissue during implantation. A smaller tube 12 fits over the trocar 16, such that the trocar can position and set the tube 12. The tube 12 has a longitudinal slot 30 down its entire length which allows greater sensitivity to small loads and protects the apparatus from overloading, and allows the key 13 to engage and control the tube 12 during the implantation. Bonded to the wall of the tube 12 is at least one strain gauge sensor 15 and 15a, which are normally piezo-resistive type strain gauges. This sensor is wired directly to equipment that measures and displays the tension on the gauge that is caused by the squeezing of the tube 12 once the trocar 16 and the outer cannulae 11 are removed. The sensors 15 and 15a can be positioned on the inside, as well as the outside of the tube 12. This will effectively double the sensor's sensitivity because the inside gauge is loaded in compression and the outside gauge is loaded in tension; when the tube is deformed inward. A small fin 14 on the outer side of the inner tube 12 keeps the tube 12 and the strain gauges 15 and 15a aligned in the tissue once the apparatus is set in position. The end of cannulae 11 fits snugly against the tube 12, which allows the main guide cannulae 11 to act as a buttress against the tube 12. A tapered sleeve 17 is positioned at the bottom of the inner tube 12 to prevent the apparatus from backing out the of the tissue. A guide arrow 18 at the top of the main guide cannulae 11 points out the position of the key 13 and the longitudinal slot 30. The arrow is used during implantation to insure reproducible alignment of the apparatus. The tube 12 is designed to use stainless steel tubing or other product that is biocompatible and strong and can be made of varying sizes for each desired purpose. The wall thickness of the tube 12 may be varied to change the physical characteristics for improved dynamic response, and the sensitivity to load, by altering the stiffness of the device. The circuitry is connected to the strain gauge 15 by wired leads 19, 19a and 19b. By way of example, a wheatstone bridge 20 is comprised of a single active element, that is the sensing element and a number of resistive elements that may be located external to the implantable device. Alternatively, additional gauges may be bonded to the tube 12 to enhance sensitivity to pressure and to reduce sensitivity to temperature. In this case, the tube 12 may be formed so that a small longitudinal pocket 29 on the inside of the tube 12 permits a strain gauge 15a to be bonded on the inner wall of the tube 12 and be protected, without interference or damage from the trocar 16. Strain gauge 15a is loaded in compression and gauge 15 in tension when the trocar 16 is removed and tissue squeezes on the walls of the tube 12. The configuration of the wheatstone bridge can be modified to accommodate additional gauges bonded to the tube 12. Excitation of the bridge is accomplished by the use of a regulated voltage or current source 21. A change in resistance of the sensing element will produce an imbalance in the bridge which is monitored by the signal conditioner 22 and displayed by the display unit 23. An alternative embodiment would be to use an implantable telemetry device which would allow remote and untethered monitoring of data from the implanted sensor.

The novel method comprises the steps of:

providing the main guide cannulae which has an alignment key formed therein;

providing a retractable trocar;

inserting the retractable trocar within the main guide cannulae;

providing tubular means which has a sensing means attached thereto;

emplacing the tubular means over the trocar;

positioning the alignment key in the longitudinal slot of said tubular means;

pressing the trocar and the inner tube at the desired position of the soft tissue of the patient's body;

cuttingly penetrating the soft tissue of the patient's body with said trocar and said tubular means until the desired depth, at which to implant the sensing means, has been reached; and using the cannulae as a buttressing element during the penetrating step; wherein said cannulae has a positioning arrow at one end thereof; and maintaining a proper positioning of the cannulae and alignment projection of the tubular means by reference to the arrow;

removing the trocar from the cannulae; and removing the cannulae.

In operation, the user can calibrate the apparatus by squeezing the sensor in a mechanical forcing frame, under known loads per unit area, and then relating the device output to a known measured input. If the user desires to measure tension, the lateral squeeze pressure must be related to tissue tension. This may be accomplished by applying known tension directly to the instrumented tissue, and relating this to the output of the apparatus. In some applications, it is possible to apply a known external load to the bones of a joint, and thereby produce predictable loads within the instrumented tissue. This technique can be used to relate predicted loads within the instrumented soft tissue to outputs from the implanted sensor. Once the relationship has been established, subsequent outputs from the device can be used to measure ligament loading under physiologic conditions. This information can be used to evaluate knee braces, exercise programs and in the pursuit of understanding of soft tissue behavior. Once the measurements have been be made, the apparatus can be removed by pulling on the lead wires, alternatively an additional stranded stainless steel wire can be attached to the tube in order remove the apparatus without putting a large amount of stress on the apparatus.

While I have described my invention in connection with specific embodiments thereof, it is clearly to be understood that this is done only by way of example and not as a limitation to the scope of my invention as set forth in the objects thereof and in the appended claims.

I claim:

1. An implantable pressure and force sensing apparatus, for measuring the mechanical behavior of the soft tissue of the body, comprising:

a main guide cannulae;

said main guide cannulae having an alignment key positioned at the lower end of said main guide cannulae;

said main guide cannulae further having a direction indicator at the upper end of said cannulae;

retractable centerline cutting and positioning means;

tubular means comprising means that fit over said retractable centerline cutting and positioning means;

said tubular means having at least one sensing means attached thereto;

said tubular means having a protective pocket for said at least one sensing means;

said tubular means further having a longitudinal slot for receiving said alignment key of said main guide cannulae, and extends from one end of said tubular means to the opposite end of said tubular means;

said tubular means further having an alignment projection means located at the upper end of said tubular means for maintaining said tubular means in the proper orientation within tissue;

said upper end of said tubular means being in close replaceable contact with the lower end of said main guide cannulae for the purpose of buttressing the tubular means during implantation; and said tubular means further having an enlarged tapered section at the end opposite said upper end for preventing said tubular means from backing out of the tissue.

2. An implantable pressure and force sensing apparatus, according to claim 1, wherein:
said sensing means comprises a piezo-resistive strain gauge means;
said strain gauge means having bonding means to allow said strain gauge to be attached to the surface of said tubular means.

3. An implantable pressure and force sensing apparatus, according to claim 1, wherein:
said enlarged tapered section of said tubular means comprises a flared base section that is wider at its uppermost end and narrower at its lower portion.

4. An implantable pressure and force sensing apparatus, according to claim 1, wherein:
said retractable centerline cutting means comprises a micro-trocar that can be withdrawn from said tubular means after the cut and the implantation have been made.

5. A method of implanting a pressure and force sensing apparatus into a patient's body, for use in medical and other applications, comprising the steps of:
providing a main guide cannulae which has an alignment key projecting therefrom;
providing a retractable trocar;
inserting the retractable trocar within the main guide cannulae;
providing tubular means which has a sensing means attached thereto;
providing tubular means further having a longitudinal slot therein;
emplacing the tubular means over the trocar;
protecting said sensing means from said trocar with a protective pocket;
positioning the alignment key in the longitudinal slot of said tubular means;
pressing the trocar and said tubular means at a desired position on the soft tissue of the patient's body;
cuttingly penetrating the soft tissue of a patient's body with said trocar and said tubular means until the desired depth, at which to implant the sensing means, has been reached; and
using the cannulae as a buttressing element during the penetrating step; wherein
said cannulae has a positioning arrow at one end thereof; and
maintaining a proper positioning of the cannulae and the alignment projection of the tubular means by reference to the arrow;
removing the trocar from the cannulae; and
removing the cannulae.

* * * * *